United States Patent

Diehr et al.

[11] Patent Number: 4,732,711
[45] Date of Patent: Mar. 22, 1988

[54] HERBICIDAL NOVEL 1-(2-TRIFLUOROMETHOXY-PHENYLSULPHONYL)-3-HETEROARYL-(THIO)UREAS

[75] Inventors: Hans-Joachim Diehr; Christa Fest, .both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld; Hans-Joachim Santel, Cologne; Robert R. Schmidt, Bergisch Gladbach; Ludwig Eue, Leverkusen; Ernst Kysela, Bergisch Gladbach, all of Fed. Rep. of Germany

[73] Assignee: Bayer Aktiengesellschaft, Leverkusen, Fed. Rep. of Germany

[21] Appl. No.: 868,962

[22] Filed: May 30, 1986

Related U.S. Application Data

[62] Division of Ser. No. 769,186, Aug. 23, 1986.

[30] Foreign Application Priority Data

Aug. 30, 1984 [DE] Fed. Rep. of Germany ..... 34319174

[51] Int. Cl.⁴ .................. C07C 154/00; C07D 251/02
[52] U.S. Cl. ................ 260/545 R; 544/211; 544/321; 544/332
[58] Field of Search .......... 564/91; 544/211; 260/545 R

[56] References Cited

U.S. PATENT DOCUMENTS 4,379,769  4/1983  Levitt ............... 260/545 R 4,452,628  6/1984  Adams ............... 544/211

Primary Examiner—Alan Siegel
Attorney, Agent, or Firm—Sprung Horn Kramer & Woods

[57] ABSTRACT

1-(2-Trifluoromethoxy-phenylsulphonyl)-3-heteroaryl-(thio)urea herbicides of the formula

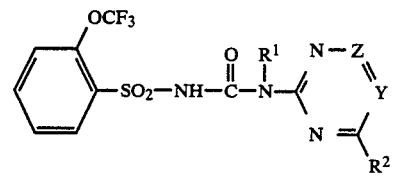

in which
Q represents oxygen or sulphur,
$R^1$ represents hydrogen, $C_1$-$C_4$-alkyl or benzyl,
$R^2$ represents hydrogen, halogen, hydroxyl, $C_1$-$C_4$-alkyl, $C_1$-$C_4$-halogenoalkyl, $C_1$-$C_4$-alkoxy, $C_1$-$C_4$-halogenoalkoxy, $C_1$-$C_4$-alkylthio, $C_1$-$C_4$-halogenoalkylthio, amino, $C_1$-$C_4$-alkylamino or di-($C_1$-$C_4$-alkyl)-amino,
X represents nitrogen or a —CH— grouping,
Y represents nitrogen or a —$CR^3$— grouping, wherein
$R^3$ represents hydrogen, halogen, $C_1$-$C_4$-alkyl, ($C_1$-$C_2$-alkyl)-carbonyl or ($C_1$-$C_2$-alkoxy)-carbonyl, and
Z represents nitrogen or a —$CR^4$— grouping, wherein
$R^4$ represents hydrogen, halogen, hydroxyl, $C_1$-$C_4$-alkyl, $C_1$-$C_4$-alkoxy, $C_1$-$C_4$-alkylthio, $C_1$-$C_4$-alkylamino or di-($C_1$-$C_4$-alkyl)-amino.

1 Claim, No Drawings

HERBICIDAL NOVEL 1-(2-TRIFLUOROMETHOXY-PHENYLSULPHONYL)-3-HETEROARYL-(THIO)UREAS

This is a division of application Ser. No. 769,186, filed Aug. 23, 1986, now pending.

The invention relates to new 1-(2-trifluoromethoxy-phenylsulphonyl)-3-heteroaryl-(thio)urea, several processes for their preparation and their use as herbicides.

It is known that certain 1-arylsulphonyl-3-heteroaryl-ureas, such as, for example, 1-(2-methoxy-phenylsulphonyl)-3-(4,6-dimethyl-pyrimidin-2-yl)-urea, have a herbicidal action. However, the action of these compounds is not always completely satisfactory (compare U.S. Pat. No. 4,169,719).

New 1-(2-trifluoromethoxy-phenylsulphonyl)-3-heteroaryl-(thio)ureas of the general formula (I)

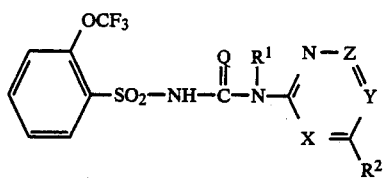

in which

Q represents oxygen or sulphur, $R^1$ represents hydrogen, $C_1$–$C_4$-alkyl or benzyl, $R^2$ represents hydrogen, halogen, hydroxyl, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, amino, $C_1$–$C_4$-alkylamino or di-($C_1$–$C_4$-alkyl)-amino, X represents nitrogen or a —CH— grouping, Y represents nitrogen or a —$CR^3$— grouping, wherein $R^3$ represents hydrogen, halogen, $C_1$–$C_4$-alkyl, ($C_1$–$C_2$-alkoxy)-carbonyl, and ($C_1$–$C_2$-alkyl)-carbonyl and Z represents nitrogen or a —$CR^4$— grouping, wherein $R^4$ represents hydrogen, halogen, hydroxyl, $C_1$–$C_4$-alkyl, $C_1$–$C_4$-alkoxy, $C_1$–$C_4$-alkylthio, $C_1$–$C_4$-alkylamino or di-($C_1$–$C_4$-alkyl)-amino, have now been found.

The new 1-(2-trifluoromethoxy-phenylsulphonyl)-3-heteroaryl-(thio)ureas of the formula (I) are obtained by a process in which (a) 2-trifluoromethoxy-phenylsulphonyl iso(thio)cyanates of the formula (II)

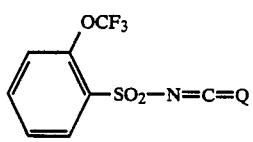

in which Q represents oxygen or sulphur, are reacted with heteroarylamines of the formula (III)

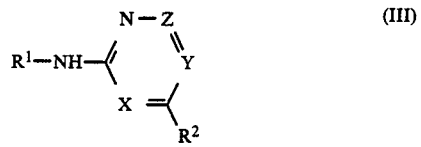

in which $R^1$, $R^2$, X, Y and Z have the abovementioned meanings, if appropriate in the presence of diluents and if appropriate in the presence of catalysts, or (b) 2-trifluoromethoxy-benzenesulphonic acid amide of the formula (IV)

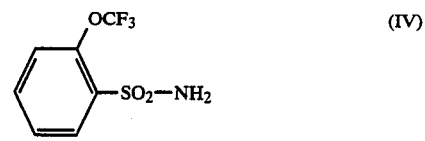

is reacted with N-heteroaryl-urethanes of the formula (V)

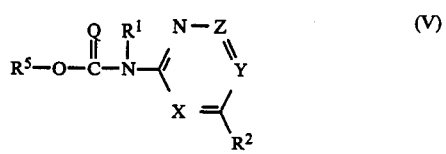

in which $R^1$, $R^2$, Q, X, Y and Z have the abovementioned meanings and $R^5$ represents $C_1$–$C_4$-alkyl, benzyl or phenyl, if appropriate in the presence of diluents and if appropriate in the presence of acid acceptors, or (c) N-(2-trifluoromethoxy-phenylsulphonyl)-urethanes of the formula (VI)

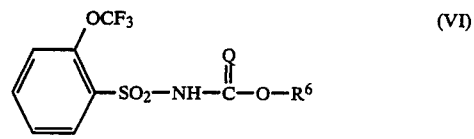

in which

Q represents oxygen or sulphur and $R^6$ represents $C_1$–$C_4$-alkyl, benzyl or phenyl, are reacted with heteroarylamines of the formula (III)

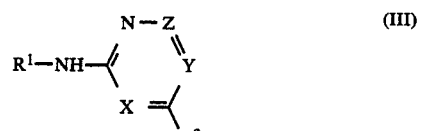

in which $R^1$, $R^2$, X, Y and Z have the abovementioned meanings, if appropriate in the presence of diluents and if appropriate in the presence of acid acceptors.

The new 1-(2-trifluoromethoxy-phenylsulphonyl)-3-heteroaryl-(thio)ureas of the formula (I) are distinguished by a powerful herbicidal activity.

Surprisingly, the new compounds of the formula (I) exhibit a considerably better herbicidal action than the previously known urea derivatives of the same type of action.

The invention preferably relates to compounds of the formula (I) in which

Q represents oxygen, $R^1$ represents hydrogen or methyl, $R^2$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, X represents nitrogen or a —CH— grouping, Y represents nitrogen or a —$CR^3$— grouping, wherein $R^3$ represents hydrogen, fluorine, chlorine, bromine, methyl or acetyl, and Z represents nitrogen or a —$CR^4$— grouping, wherein $R^4$ represents hydrogen, fluorine, chlorine, bromine, methyl, ethyl, methoxy, ethoxy, propoxy, isopropoxy, methylthio, ethylthio, methylamino, ethylamino, dimethylamino or diethylamino.

The invention particularly relates to compounds of the formula (I) in which

Q represents oxygen, $R^1$ represents hydrogen, $R^2$ represents methyl, methoxy, ethoxy or dimethylamino, X represents nitrogen, Y represents nitrogen or a —$CR^3$— grouping, wherein $R^3$ represents hydrogen, and Z represents a —$CR^4$— grouping, wherein $R^4$ represents hydrogen, methyl, methoxy or ethoxy.

If, for example, 2-trifluoromethoxy-phenylsulphonyl isothiocyanate and 2-amino-4-ethoxy-6-methyl-s-triazine are used as starting substances for process variant (a), the course of the reaction can be outlined by the following equation:

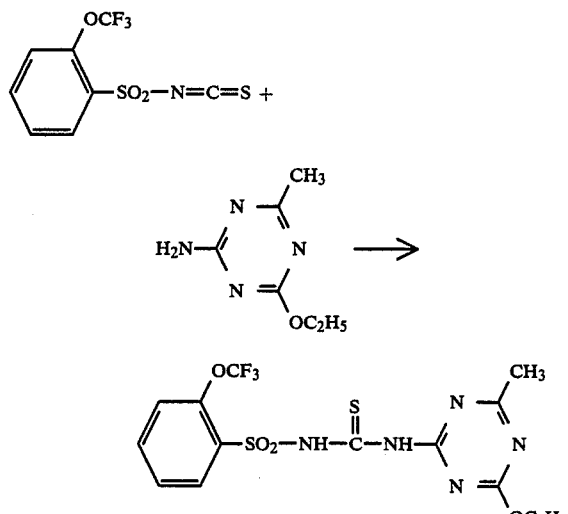

If, for example, 2-trifluoromethoxy-benzenesulphonic acid amide and O-phenyl-N-(4-ethylamino-6-methylthio-s-triazin-2-yl)-urethane are used as starting substances for process variant (b), the course of the reaction can be outlined by the following equation:

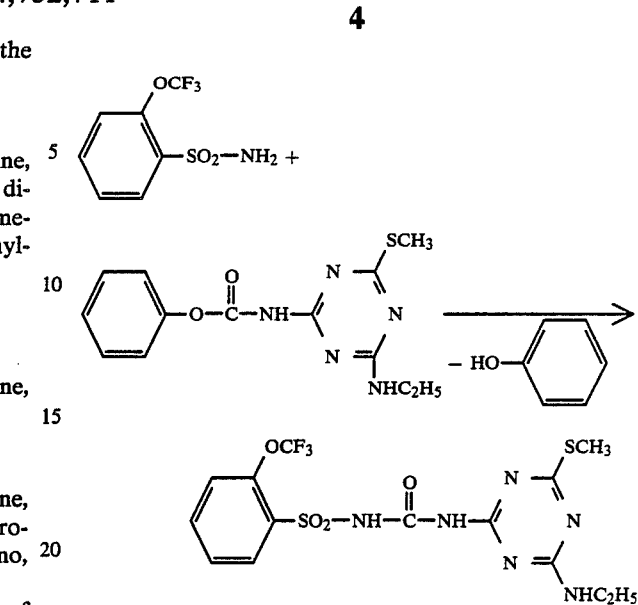

If, for example, O-phenyl-N-(2-trifluoromethoxyphenylsulphonyl)-urethane and 2-amino-4-chloro-6-methoxypyrimidine are used as starting substances for process variant (c), the course of the reaction can be outlined by the following equation:

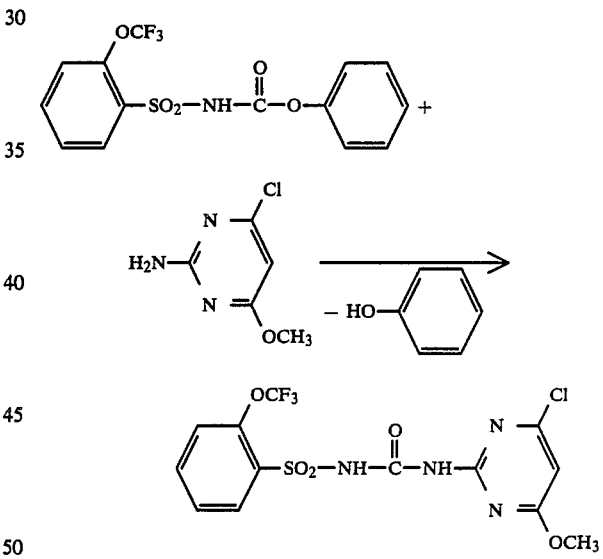

Formula (II) provides a definition of the 2-trifluoromethoxy-phenylsulphonyl iso(thio)cyanates to be used as starting substances for process variant (a). In formula (II), Q preferably and particularly has the same meaning as is given above as preferred or as particularly preferred in the context of the definition of the substituents for formula (I).

Examples of compounds of the formula (II) which may be mentioned are 2-trifluoromethoxy-phenylsulphonyl isocyanate and 2-trifluoromethoxy-phenylsulphonyl isothiocyanate.

The compounds of the formula (II) have not yet been described in the literature. The compound of the formula (II) in which Q represents oxygen is obtained by a process in which 2-trifluoromethoxy-benzenesulphonic acid amide of the formula (IV)

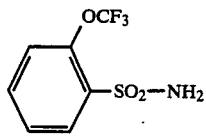

is reacted with thionyl chloride at temperatures between 50° C. and 100° C., and the product is then reacted with phosgene, if appropriate in the presence of a diluent, such as, for example, toluene, and if appropriate in the presence of a catalyst, such as, for example, pyridine, at temperatures between 50° C. and 120° C. (compare J. Org. Chem. 34 (1969), 3200).

The compound of the formula (II) in which Q represents sulphur is obtained by a process in which 2-trifluoromethoxy-benzenesulphonic acid amide of the formula (IV) is reacted with carbon disulphide in the presence of an acid acceptor, such as, for example, potassium hydroxide, and if appropriate in the presence of a diluent, such as, for example, dimethylformamide, at temperatures between 0° C. and 50° C., and the product is then reacted with phosgene or thionyl chlorine, if appropriate in the presence of a diluent, such as, for example, methylene chlorine, at temperatures between 0° C. and 50° C. (compare Arch. Pharm. 299 (1966), 174).

Formula (III) provides a general definition of the heteroarylamines also to be used as starting substances for process variant (a). In formula (III), $R^1$, $R^2$, X, Y and Z preferably and particularly have the same meanings as are given above as preferred or as particularly preferred in the context of the definition of the substituents for formula (I).

Examples which may be mentioned of compounds of the formula (III) are: 4,6-dimethyl-, 4-methoxy-6-methyl-, 4-ethoxy-6-methyl- and 4,6-dimethoxy-2-aminopyrimidine, 4,6-dimethyl-, 4-methoxy-6-methyl-, 4-ethoxy-6-methyl- and 4,6-dimethoxy-2-amino-s-triazine and 5,6-dimethyl-2-amino-1,3,4-triazine.

the compounds of the formula (III) are known and can be prepared by processes which are known per se (compare Chem. Pharm. Bull. 11 (1963), 1382 and U.S. Pat. No. 4,299,960).

The 2-trifluoromethoxy-benzenesulphonic acid amide of the formula (IV) to be used as a starting substance for process variant (b) is already known (compare Zh. Org. Khim. [J. Org. Chem. USSR], 8 (1972), 1023–1026 [English 1032–1034]).

Formula (V) provides a general definition of the N-heteroaryl-urethanes also to be used as starting substances in process (b). In formula (V), $R^1$, $R^2$, X, Y and Z preferably and particularly have the same meanings as are given above as preferred or as particularly preferred in the context of the definition of the substituents for formula (I); furthermore, Q preferably represents oxygen and $R^5$ represents methyl, benzyl or phenyl, in particular methyl or phenyl.

Examples which may be mentioned of compounds of the formula (V) are: N-(4,6-dimethyl-pyrimidin-2-yl)-, N-(4-methoxy-6-methyl-pyrimidin-2-yl)-, N-(4-ethoxy-6-methyl-pyrimidin-2-yl)-, N-(4,6-dimethoxy-pyrimidin-2-yl)-, N-(4,6-dimethyl-s-triazin-2-yl)-, N-(4-methoxy-6-methyl-s-triazin-2-yl)-, N-(4-ethoxy-6-methyl-s-triazin-2-yl)-, N-(4,6-dimethoxy-s-triazin-2-yl)- and N-(5,6-dimethyl-1,3,4-triazin-2-yl)-O-methyl-urethane and O-phenyl-urethane.

The compounds of the formula (V) are known and can be prepared by processes which are known per se (compare EP-OS (European Published Specification No. 101,670).

Formula (VI) provides a general definition of the N-(2-trifluoromethoxy-phenylsulphonyl)-urethanes to be used as starting substances for process variant (c). Preferably, in formula (VI), Q represents oxygen and $R^6$ represents methyl, benzyl or phenyl, in particular methyl or phenyl.

Examples which may be mentioned of compounds of the formula (VI) are: N-(2-trifluoromethoxy-phenylsulphonyl)-O-methyl-urethane and N-(2-trifluoromethoxy-phenylsulphonyl)-O-phenyl-urethane.

The compounds of the formula (VI) are not yet described in the literature. These compounds are obtained by a process in which 2-trifluoromethoxy-benzenesulphonic acid amide of the formula (IV) is reacted with compounds of the formula (VII)

in which
Q and $R^6$ have the abovementioned meanings and
A represents chlorine or phenoxy,
if appropriate in the presence of acid acceptors, such as, for example, sodium hydride, potassium tert.-butylate or diazabicycloundecene (DBU), and if appropriate in the presence of diluents, such as, for example, acetonitrile or dimethylformamide, at temperatures between 0° C. and 50° C. (compare EP-OS (European Published Specification) 101,407).

The starting substances of the formulae (IV) and (VII) are known.

The preparation process described above under (a) for the compounds of the formula (I) is preferably carried out in the presence of diluents. Possible diluents are virtually all the inert organic solvents. These include, in particular, aliphatic or aromatic, optionally halogenated hydrocabons, such as, for example, pentane, hexane, heptane, benzine, petroleum ether, ligroin, cyclohexane, benzene, toluene, xylene, chlorobenzene, methylene chloride, chloroform and carbon tetrachloride, ethers, such as diethyl ether, diisopropyl ether, tetrahydrofuran, 1,2-dimethoxyethane and dioxane, ketones, such as acetone, methyl ethyl ketone and methyl isobutyl ketone, nitriles, such as acetonitrile and propionitrile, esters, such as methyl acetate and ethyl acetate, amides, such as dimethylformamide and dimethylacetamide, and dimethylsulphoxide.

If appropriate, process (a) is carried out in the presence of a catalyst. Catalysts include, in particular, aliphatic, aromatic or heterocyclic amines, such as triethylamine, N,N-diethylaniline, pyridine, 2-methyl-5-ethyl-pyridine, 4-dimethylamino-pyridine, diazabicyclooctane (DABCO), diazabicyclononene (DBN) and diazabicycloundecene (DBU).

The reaction temperature can be varied within a substantial range in a process (a). In general, the reaction is carried out at temperatures between 0° C. and 150° C., preferably between 20° C. and 100° C.

For carrying out process (a) according to the invention, in general 1.0 1.5 moles, preferably 1.0 to 1.2 moles, of 2-trifluoromethoxy-phenylsulphonyl iso(thio)cyanate of the formula (II) are employed per mole of heteroarylamine of the formula (III).

The starting substances of the formulae (II) and (III) and, if appropriate, the catalyst and the diluent are in general brought together at room temperature or with gentle external cooling, and the reaction mixture is stirred, if appropriate at elevated temperature, until the reaction has ended.

The new compounds of the formula (I) are worked up and isolated by customary methods: if the compounds of the formula (I) are obtained as crystals, they are isolated by filtration with suction. Otherwise—if appropriate after concentration—water and an organic solvent which is virtually water-immiscible are added and, after thorough shaking, the organic phase is separated off, dried, filtered and concentrated, the products of the formula (I) remaining in the residue.

The preparation process described above under (b) for the compounds of the formula (I) is preferably carried out in the presence of diluents. Possible diluents here are the same organic solvents as have been mentioned above in connection with the description of process (a) according to the invention.

Process (b) is preferably carried out in the presence of an acid acceptor. Possible acid acceptors are all the usual inorganic acid-binding agents and organic bases. These include, for example, alkali metal and alkaline earth metal hydroxides, such as sodium hydroxide, potassium hydroxide and calcium hydroxide, alkali metal and alkaline earth metal carbonates, such as sodium carbonate, potassium carbonate and calcium carbonate, and aliphatic, aromatic and heterocyclic amines, such as triethylamine, N,N'-dimethylaniline, N,N-dimethyl-benzylamine, pyridine, 2-methyl-5-ethyl-pyridine, 4-dimethyl-amino-pyridine, diazabicyclooctane (DABCO), diazabicyclononene (DBN) and diazabicycloundecene (DBU).

The reaction temperature can be varied within a substantial range in process (b). In general, the reaction is carried out at temperatures between <20° C. and +100° C., preferably between 0° C. and 50° C.

For carrying out process (b) according to the invention, in general 1.0 to 1.5 moles, preferably 1.0 to 1.2 moles, of 2-trifluoromethoxy-benzenesulphonic acid amide of the formula (IV) are employed per mole of N-heteroaryl-urethane of the formula (V).

The starting substances of the formulae (IV) and (V) and, if appropriate, the acid acceptor and the diluent are in general brought together at room temperature or with gentle external cooling, and the reaction mixture is stirred, if appropriate at elevated temperature, until the reaction has ended. The new compounds of the formula (I) can be worked and isolated by cutomary meethods: in general—if appropriate after concentration—the mixture is stirred with water and, if appropriate, acidified with hydrochloride acid. If the compounds of the formula (I) are obtained as crystals here, they are isolated by filtration with suction. Otherwise, the mixture is extracted with a solvent which is virtually water-immiscible, such as, for example, ethyl acetate or methylene chloride, and the organic phase is separated off, dried, filtered and concentrated, the products of the formula (I) remaining in the residue.

The preparation process described above under (c) for the compounds of the formula (I) is preferably carried out in the presence of diluents. Possible diluents here are the same organic solvents as have been mentioned above in connection with the description of the process (a) according to the invention.

Process (c) is preferably carried out in the presence of an acid acceptor. Possible acid acceptors here are the same inorganic acid-binding agents and organic bases which have been mentioned above in connection with the description of process (b) according to the invention.

The reaction temperature can be varied within a substantial range in process (c). In general, the reaction is carried out at temperatures between −20° C. and +100° C., preferably between 0° C. and 50° C.

To carry out process (c) according to the invention, in general 1.0 to 1.5 moles, preferably 1.0 to 1.2 moles, of heteroarylamine of the formula (III) are employed per mole of N-(2-trifluoromethoxy-phenylsulphonyl)-urethane of the formula (VI).

The procedure and working up in process (c) can be as described above for process (b).

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially in the amount used.

The active compounds according to the invention can be used, for example, in connection with the following plants:

Dicotyledon weeds of the genera: sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleium, Poa, Festuca, Eleusine, Brachiaria, Lolium, Bromus, Avena, Cyperus, Sorghum, Agropyron, Cynodon, Monochloria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil plam plantations, cocoa plantations, soft fruit plantings and hopfields, and for the selective combating of weeds in annual cultures.

The active compounds according to the invention can be used by the pre-emergence or post-emergence method for combating monocotyledon and dicotyledon weeds.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compounds, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocabons, such as chlorobenzenes, chloroethylenes or methylene chloride, aliphatic hydrocarbons, such as cyclohexane or paraffins, for example petroleum fractions, mineral and vegetable oils, alcohols, such as butanol or glycerol as well as their ethers and esters, ketones, such as acetone, methyl ethyl ketone, methyl isobutyl butyl ketone or cyclohexanone, strongly polar solvents, such as dimethylformamide and dimethylsulphoxide, as well as water.

As solid carriers there are suitable: for example ammonium salts and ground natural minerals, such as kalolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as clacite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, anu organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of thier formulations, can also be used, for combating weeds, as mixtures with known herbicides, finished formulations or tank mixes being possible.

Mixtures with known herbicides, include, for example, N-(2-benzothiazolyl)-N,N'-dimethylurea, 3-(3-chloro-4-methylphenyl)-1,1-dimethylurea, 3-(4-isopropylphenyl)-1,1-dimethylurea, 4-amino-6-(1,1-dimethyl-ethyl)-3-methylthio-1,2,4-triazin-5(4H)-one, 4-amino-6-(1,1-dimethyl-ethyl)-3-ethylthio-1,2,4-triazin-5(4H)-one, 1-amino-6-ethylthio-3-(2,2-dimethylpropyl)1,3,5-triazin-2,4-(1H,3H)-dione, 4-amino-3-methyl-6-phenyl-1,2,4-triazin-5(4H)-one, 2-chloro-4-ethylamino-6-isopropylamino-1,3,5-triazine, the R-enantiomer of (trimethylsilyl)-methyl 2-[4-(3,5-dichloropyridin-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxy-acetic acid, 2-(2,4-dichlorophenoxy)-propionic acid, 4-chloro-2-methyl-phenoxy-acetic acid, 2-(2-methyl-4-chlorophenoxy)-propionic acid, 3,5-diiodo-4-hydroxy-benzonitrile, 3,5-dibromo-4-hydroxy-benzonitrile and diphenyl ether and phenylpyridazines, such as, for example, pyridates, 2-chloro-N-(2-ethyl-6-methyl-phenyl)-N-(2-methoxy-1-methylethyl)-acetamide, 2-chloro-N-(2,6-diethylphenyl)-N-(methoxymethyl)-acetamide, 2-(2-benzothiazolyloxy)-N-methyl-N-phenylacetamide, N-phosphonomethylglycine and 3-(1-methylethyl)-1H-2,1,3-benzothiadiazin-4(3H)-one 2,2-dioxide. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 10 kg active compound per hectare of soil surface, preferably between 0.05 and 5 kg per ha.

The preparation and use of the active compounds according to the invention can be seen from the following examples.

Preparation Examples

EXAMPLE 1

(Process (a))

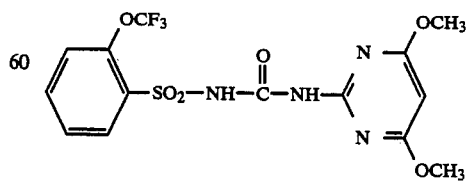

A solution of 28 g (0.11 mole) of 2-trifluoromethoxyphenylsulphonyl isocyanate in 30 ml of toluene is added dropwise to a mixture of 15.5 g (0.10 mole) of 2-amino- 4,6-dimethoxy-pyrimidine and 100 ml of acetonitrile at 20° C., with stirring, and the reaction mixture is stirred at 60° C. for 2 hours. After cooling, the product obtained as crystals is isolated by filtration with suction.

20.7 g (49% of theory) of 1-(2-trifluoromethoxy-phenylsulphonyl)-3-(4,6-dimethoxy-pyrimidin-2-yl)-urea of melting point 170° C. are obtained.

EXAMPLE 2

(Process (b))

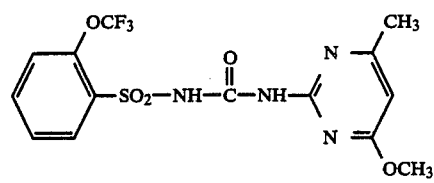

2.5 g (0.022 mole) of potassium tert.-butanolate are added in portions to a mixture of 4.0 g (0.019 mole) of 2-trifluoromethoxybenzenesulphonic acid amide, 5.0 g (0.019 mole) of N-(4-methoxy-6-methyl-pyrimidin-2-yl)-O-phenyl-urethane and 50 ml of acetonitrile at 20° C. to 30° C., with stirring. The mixture is then concentrated, the residue is taken up in 30 ml of water and the mixture is acidified with concentrated hydrochloric acid. The product thereby obtained as crystals is isolated by filtration with suction.

1.2 g (15% of theory) of 1-(2-trifluoromethoxy-phenylsulphonyl)-3-(4-methoxy-6-methyl-pyrimidin-2-yl)urea of melting point 162° C. are obtained.

The compounds of the formula (I) listed in Table 1 below can be prepared by the processes described by way of example in the preceding examples:

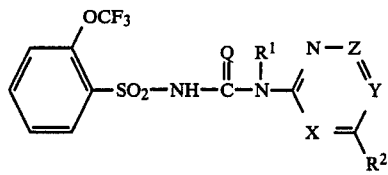
(I)

Preparation of starting substances of the formula (II)

EXAMPLE (II-1)

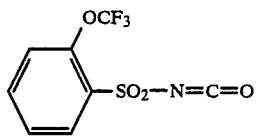

Somewhat more than the stoichiometric amount of ammonia is introduced into a solution of 260 g (1.0 mole) of 2-trifluoromethoxybenzenesulphonyl chloride in 2 ml of tetrahydrofuran at 30° C. As soon as the precipitation of ammonium chloride has ended, the mixture is concentrated, the residue is suspended in 2 l of ethyl acetate and the mixture is washed with 1 l of water. The organic phase is dried, filtered and concentrated. The residue is stirred with about 500 ml of hexane and the product thereby obtained as crystals is isolated by filtration with suction.

220 g (91% of theory) of 2-trifluoromethoxybenzenesulphonic acid amide of melting point 186° C. are obtained.

220 g (0.91 mole) of 2-trifluoromethoxy-benzene-sulphonic acid amide are taken up in 1.5 l of thionyl chloride and, after addition of 5 ml of dimethylformamide, the reaction mixture is heated at the boiling point under reflux, until the evolution of gas has virtually ended. The mixture is then concentrated, the residue is taken up in 500 ml of toluene containing 2.5 ml of pyridine, and 160 g (1.6 moles) of phosgene are added. After the mixture has been heated under reflux for 3 hours, it is concentrated.

225 g (93% of theory) of 2-trifluoromethoxyphenyl-sulphonyl isocyanate are obtained as a viscous oil which is further processed as a crude product.

EXAMPLE (II-2)

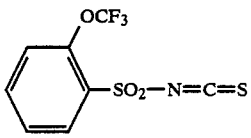

24.1 g (0.1 mole) of 2-trifluoromethoxy-benzene-sulphonic acid amide are dissolved in 100 ml of dimethylformamide. 7.6 g (0.1 mole) of carbon disulphide and 5.6 g (0.1 mole) of potassium hydroxide powder are added

TABLE 1

| Example No. | Q | $R^1$ | $R^2$ | X | Y | Z | Melting point (°C.) |
|---|---|---|---|---|---|---|---|
| 3 | O | H | $CH_3$ | N | CH | C—$CH_3$ | 194 |
| 4 | O | H | Cl | N | CH | C—Cl | 164 |
| 5 | O | H | $CH_3$ | N | C—$CH_3$ | N | 134 |
| 6 | O | H | $CH_3$ | N | CH | CH | 180–181 |
| 7 | O | H | $CH_3$ | CH | CH | C—$CH_3$ | 204–205 |
| 8 | O | H | $OCH_3$ | N | N | C—$CH_3$ | 162 |
| 9 | O | H | $CH_3$ | N | N | C—$CH_3$ | 171 |
| 10 | S | H | $CH_3$ | N | CH | C—$CH_3$ | |
| 11 | S | H | $OCH_3$ | N | CH | C—$OCH_3$ | |
| 12 | O | H | $OCH_3$ | N | CH | C—Cl | 158–160 |
| 13 | O | H | $CH_3$ | N | C—$COCH_3$ | CH | |
| 14 | O | H | $CH_3$ | N | N | C—$N(CH_3)_2$ | 178 (decomposition) |
| 15 | O | H | $OCH_3$ | N | N | C—$OCH_3$ | 182–183 |
| 16 | O | H | $CH_3$ | N | C—$COOC_2H_5$ | N | |
| 17 | O | H | $OC_2H_5$ | N | CH | C—$OC_2H_5$ | | and the reaction mixture is stirred at 35° C. until a clear solution has formed. A further 5.6 g (0.1 mole) of potassium hydroxide powder are then added and stirring is continued until a clear solution is formed. 100 ml of ethyl acetate are then added dropwise at 20° C. The product thereby obtained as crystals is isolated by filtration with suction and dried under reduced pressure. The dried product is suspended in 100 ml of toluene; 20 g of liquid phosgene are added dropwise at 0° C. and the mixture is stirred at 5° C. to 10° C. for one hour and at 20° C. for two hours. After filtration, the filtrate is concentrated to give an oily residue, which essentially contains 2-trifluoromethoxy-phenylsulphonyl isothiocyanate. Because of its low stability, the product is reacted as quickly as possible—without further purification—in the process according to the invention.

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, the active compounds according to the invention exhibit a very good herbicidal activity, especially the compounds from preparation Examples 1, 2, 3, 5, 8.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, the active compounds according to the invention exhibit a very good herbicidal activity, especially the compounds from preparation Examples 1, 2, 3, 5, 8.

It will be understood that the specification and examples are illustrative but not limitative of the present invention and that other embodiments within the spirit and scope of the invention will suggest themselves to those skilled in the art.

We claim:

1. The compound 2-trifluoromethoxy-phenylsulphonyl isocyanate of the formula

[Chemical structure: benzene ring with OCF$_3$ substituent at position 2 and $-SO_2-N=C=O$ substituent]

* * * * *

UNITED STATES PATENT AND TRADEMARK OFFICE
CERTIFICATE OF CORRECTION

PATENT NO. : 4,732,711

DATED : March 22, 1988

INVENTOR(S) : Hans-Joachim Diehr, et al

Page 1 of 2

It is certified that error appears in the above-identified patent and that said Letters Patent is hereby corrected as shown below: On the title page:

| | |
|---|---|
| Under "Foreign Application Priority Data" | Delete "34319174" and substitute --3431917.4-- |
| Abstract, line 3 | Middle of formula delete $\overset{O}{\underset{\|}{C}}$ and substitute -- $\overset{O}{\underset{\|}{C}}$ -- |
| Col. 6, line 61 | Before "process" delete "a" |
| Col. 6, line 65 | After "1.0" insert --to-- |
| Col. 7, line 52 | After "worked" insert --up-- |
| Col. 7, line 52 | Correct spelling of --methods-- |
| Col. 7, line 55 | Delete "hydrochloride" and substitute --hydrochloric-- |
| Col. 7, line 68 | After "of" delete "the" |
| Col. 8, line 25 | After "essentially" delete "in" and substitute --on-- |
| Col. 8, line 29 | Delete "sinapis" and substitute --Sinapis-- |
| Col. 8, line 41 | Correct spelling of --Phleum-- |
| Col. 9, line 23 | Delete "glycerol" and subsittute --glycol-- |
| Col. 9, line 65 | Correct spelling of --their-- |

UNITED STATES PATENT AND TRADEMARK OFFICE
CERTIFICATE OF CORRECTION

PATENT NO. : 4,732,711
DATED : March 22, 1988
INVENTOR(S) : Hans-Joachim Diehr, et al It is certified that error appears in the above-identified patent and that said Letters Patent is hereby corrected as shown below:

Col. 12, line 14          Delete "2 ml" and substitute
                          --2 1--

Signed and Sealed this

Eighth Day of November, 1988

Attest:

DONALD J. QUIGG

Attesting Officer                Commissioner of Patents and Trademarks